US008512637B2

(12) United States Patent
Zeijlstra et al.

(10) Patent No.: US 8,512,637 B2
(45) Date of Patent: Aug. 20, 2013

(54) DEVICE FOR CUTTING A SAMPLE CARRIER

(75) Inventors: Harmina Zeijlstra, Eindhoven (NL); Ronald De Gier, Eindhoven (NL); Marloes M. E. B. Van De Wal, Eindhoven (NL); Ronaldus M. H. Steyvers, Eindhoven (NL); Astrid E. Visser, Eindhoven (NL)

(73) Assignee: Biocartis SA, Lausanne (CH)

( * ) Notice: Subject to any disclaimer, the term of this patent is extended or adjusted under 35 U.S.C. 154(b) by 0 days.

(21) Appl. No.: 13/289,534

(22) Filed: Nov. 4, 2011

(65) Prior Publication Data

US 2012/0282616 A1 Nov. 8, 2012

Related U.S. Application Data

(63) Continuation of application No. PCT/CH2010/000119, filed on May 5, 2010.

(51) Int. Cl.
*G01N 15/06* (2006.01)
*G01N 33/00* (2006.01)
*G01N 33/48* (2006.01)
*G01N 21/75* (2006.01)
*G01N 31/22* (2006.01)
*B01L 3/00* (2006.01)
*B65D 83/10* (2006.01)
*A61M 35/00* (2006.01)

(52) U.S. Cl.
USPC .......... 422/68.1; 422/406; 422/411; 206/361; 604/1; 73/864.91

(58) Field of Classification Search
USPC ............... 422/68.1, 511; 73/864.63
See application file for complete search history.

(56) References Cited

U.S. PATENT DOCUMENTS

| | | | |
|---|---|---|---|
| 3,607,134 A | 9/1971 | McIntyre | |
| 3,633,877 A | 1/1972 | Bodine | |
| 3,638,644 A * | 2/1972 | Reick | 600/191 |
| 4,212,215 A | 7/1980 | Buys | |
| 4,256,697 A | 3/1981 | Baldwin | |
| 4,371,498 A | 2/1983 | Scordato et al. | |
| 4,571,087 A | 2/1986 | Ranney | |

(Continued)

FOREIGN PATENT DOCUMENTS

| | | |
|---|---|---|
| CH | 667599 A5 | 10/1988 |
| DE | 19820466 A1 | 11/1999 |

(Continued)

OTHER PUBLICATIONS

International Search Report dated Jul. 1, 2010 from PCT/CH/2010/000119.

*Primary Examiner* — Jill Warden
*Assistant Examiner* — Julie Tavares
(74) *Attorney, Agent, or Firm* — Kusner & Jaffe

(57) ABSTRACT

A device for receiving a sample carrier is provided. The device includes an opening for receiving part of the sample carrier and a cutter for removing a part of the sample carrier. The cutter is coupled to a lid, which is movable to allow the cutter to make an incision in the sample carrier and, at the same time, to close at least part of the opening left open after receipt of the sample carrier. The disclosure further relates to a system comprising such a device and a method for operating such a device.

25 Claims, 5 Drawing Sheets

(56) References Cited

U.S. PATENT DOCUMENTS

| | | | |
|---|---|---|---|
| 4,849,340 A | 7/1989 | Oberhardt |
| 4,857,274 A | 8/1989 | Simon |
| 4,857,453 A | 8/1989 | Ullman et al. |
| 4,874,137 A | 10/1989 | Chiba |
| 4,943,522 A | 7/1990 | Eisinger et al. |
| 4,965,047 A | 10/1990 | Hammond |
| 4,983,523 A | 1/1991 | Li et al. |
| 5,004,583 A | 4/1991 | Guruswamy et al. |
| 5,096,669 A | 3/1992 | Lauks et al. |
| 5,133,937 A | 7/1992 | Frackleton et al. |
| 5,147,609 A | 9/1992 | Grenner |
| 5,219,526 A | 6/1993 | Long |
| 5,229,580 A | 7/1993 | Chioniere |
| 5,296,374 A | 3/1994 | Culshaw et al. |
| 5,397,537 A | 3/1995 | Kanda et al. |
| 5,500,187 A | 3/1996 | Deoms et al. |
| 5,504,007 A | 4/1996 | Haynes |
| 5,504,013 A | 4/1996 | Senior |
| 5,512,159 A | 4/1996 | Yoshioka et al. |
| 5,578,495 A | 11/1996 | Wilks |
| 5,589,136 A | 12/1996 | Northrup et al. |
| 5,597,532 A | 1/1997 | Connolly |
| 5,609,822 A | 3/1997 | Carey et al. |
| 5,609,823 A | 3/1997 | Harttig et al. |
| 5,622,871 A | 4/1997 | May et al. |
| 5,627,041 A | 5/1997 | Shartle |
| 5,726,026 A | 3/1998 | Wilding et al. |
| 5,746,978 A | 5/1998 | Bienhaus et al. |
| 5,770,029 A | 6/1998 | Nelson et al. |
| 5,788,928 A | 8/1998 | Carey et al. |
| 5,843,680 A | 12/1998 | Manian et al. |
| 5,856,174 A | 1/1999 | Lipshutz et al. |
| 5,882,903 A | 3/1999 | Andrevski et al. |
| 5,912,134 A | 6/1999 | Shartle |
| 5,928,880 A | 7/1999 | Wilding et al. |
| 5,928,907 A | 7/1999 | Woudenberg et al. |
| 5,945,334 A | 8/1999 | Besemer et al. |
| 5,994,056 A | 11/1999 | Higuchi |
| 6,077,669 A | 6/2000 | Little et al. |
| 6,100,084 A | 8/2000 | Miles et al. |
| 6,143,573 A | 11/2000 | Rao et al. |
| 6,210,881 B1 | 4/2001 | Little et al. |
| 6,329,139 B1 | 12/2001 | Nova et al. |
| 6,369,893 B1 | 4/2002 | Christel et al. |
| 6,391,541 B1 | 5/2002 | Petersen et al. |
| 6,426,225 B1 | 7/2002 | Lewis et al. |
| 6,431,476 B1 | 8/2002 | Taylor et al. |
| 6,440,725 B1 | 8/2002 | Pourahmadi et al. |
| 6,521,181 B1 | 2/2003 | Northrup et al. |
| 6,524,532 B1 | 2/2003 | Northrup |
| 6,551,817 B2 | 4/2003 | Besemer et al. |
| 6,565,815 B1 | 5/2003 | Chang et al. |
| 6,664,104 B2 | 12/2003 | Pourahmadi et al. |
| 6,699,711 B1 | 3/2004 | Hahn et al. |
| 6,713,297 B2 | 3/2004 | McMillan et al. |
| 6,783,736 B1 | 8/2004 | Taylor et al. |
| 6,818,185 B1 | 11/2004 | Petersen et al. |
| 6,878,540 B2 | 4/2005 | Pourahmadi et al. |
| 6,881,541 B2 | 4/2005 | Petersen et al. |
| 6,887,693 B2 | 5/2005 | McMillan et al. |
| 6,893,879 B2 | 5/2005 | Petersen et al. |
| 6,987,018 B2 | 1/2006 | Taylor et al. |
| 7,188,001 B2 | 3/2007 | Young et al. |
| 7,569,346 B2 | 8/2009 | Petersen et al. |
| 2002/0019060 A1 | 2/2002 | Petersen et al. |
| 2002/0084329 A1 | 7/2002 | Kaye et al. |
| 2004/0189311 A1* | 9/2004 | Glezer et al. ............... 324/444 |
| 2004/0200909 A1 | 10/2004 | McMillan et al. |
| 2005/0042137 A1 | 2/2005 | Petersen et al. |
| 2006/0019379 A1 | 1/2006 | Taylor et al. |
| 2006/0027686 A1 | 2/2006 | Taylor et al. |
| 2006/0030038 A1 | 2/2006 | Taylor et al. |
| 2008/0057572 A1 | 3/2008 | Petersen et al. |
| 2009/0266181 A1* | 10/2009 | Peng et al. ............... 73/864.71 |
| 2010/0068706 A1 | 3/2010 | Pourahmadi et al. |

FOREIGN PATENT DOCUMENTS

| | | |
|---|---|---|
| EP | 0271448 A2 | 6/1988 |
| EP | 0337690 A1 | 10/1989 |
| EP | 0512334 A2 | 11/1992 |
| EP | 0757830 B1 | 12/1998 |
| EP | 0706649 B1 | 1/2001 |
| EP | 1383602 B1 | 6/2006 |
| EP | 1181098 B1 | 7/2006 |
| EP | 0915173 B1 | 1/2007 |
| EP | 1179585 B1 | 7/2008 |
| FR | 2 396 628 | 2/1979 |
| GB | 938163 A2 | 10/1963 |
| GB | 2 432 420 A | 3/2007 |
| WO | 9511454 A1 | 4/1995 |
| WO | 9529473 A1 | 11/1995 |
| WO | 9838487 A2 | 9/1998 |
| WO | 9958637 A2 | 11/1999 |
| WO | 2006136990 A2 | 12/2006 |
| WO | 2009/034563 A2 | 3/2009 |
| WO | WO 2009034563 A2 * | 3/2009 |
| WO | 2010064160 A1 | 6/2010 |

\* cited by examiner

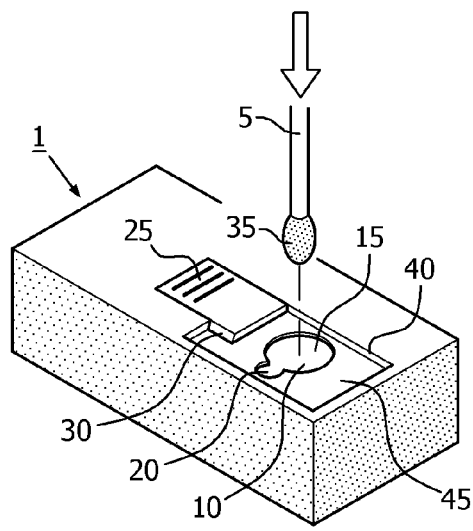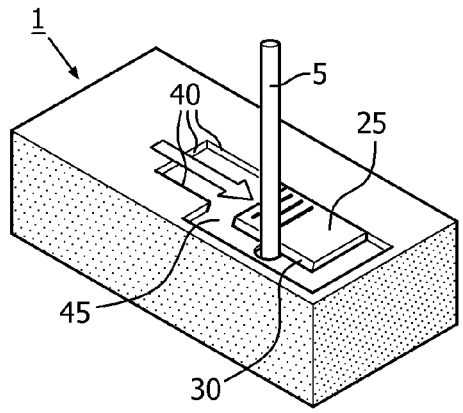
FIG. 1a          FIG. 1b
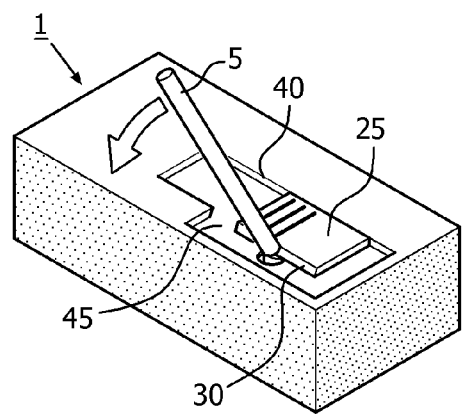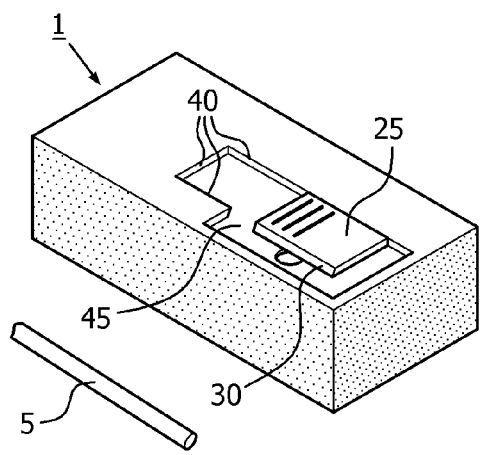
FIG. 1c          FIG. 1d

DEVICE FOR CUTTING A SAMPLE CARRIER

CROSS REFERENCE TO RELATED APPLICATIONS

This application is a continuation of International Application No. PCT/CH2010/000119 filed May 5, 2010, now pending, which claims the benefit under 35 U.S.C. §119(a) of European Patent Application No. 09159492.9, filed May 6, 2009, the entire contents of both of which are incorporated herein by reference.

BACKGROUND OF THE INVENTION

1. Field of the Invention

The present disclosure relates to a device for receiving a sample carrier. The device includes an opening for receiving part of the sample carrier; a cutter for removing a part of the sample carrier extending from the opening. The present disclosure also relates to a system comprising such a device. The present disclosure also relates to a method having the following steps: placing the sample carrier in an opening for receiving the sample carrier; and making an incision in the part of the sample carrier extending from the opening using a cutter.

2. Background of the Invention

An embodiment of a device and method of the kind mentioned above is known from US2006/0094028. This document describes a device in which the distal portion of a swab is inserted into an acquisition port after the swab has been used to obtain a target sample. The swab is inserted until the sample containing portion of the swab is substantially abutting a tip stop. The acquisition port includes a short tube that is contained within the acquisition port. There is a support block that has a mechanical severing device. The severing device moves in order to cleanly break or sever the swab. After that the swab is severed, the proximal portion of the swab is removed from the acquisition port. The severing device is moved back to its original position. Finally, the portion of the acquisition port in the remaining short tube is squeezed against a support block, thereby sealing the cartridge in which the device is comprised. It is a drawback of the known device that its operation is relatively complex requiring different steps for severing the swab and squeezing the acquisition port after the swab has been severed. This drawback is particularly significant if the device is used in an automated environment where the manipulations are performed by external instruments, as it would require more complex interactions and thus more complex systems.

SUMMARY OF THE INVENTION

It is an object of the present disclosure to provide a device and method enabling to make an incision in a sample carrier and sealing the device that are easier to use. The term incision covers both partially and completely cutting of a sample carrier. A partial cut should sufficiently weaken a sample carrier for it to be broken by an operator. Examples of suitable sample carriers are rodlike sample carriers such as, for instance, a swab, a brush, a stick, etc.

According to an aspect of the present disclosure this object is realized with a device as provided herein.

The present disclosure is based on the recognition that combining a cutter for making an incision in a sample carrier with a lid for closing the opening for receiving the sample carrier allows both to make an incision in a sample carrier and to seal the opening with a single motion. The closing motion of the lid is used to force a sample carrier and the cutter together so that the cutter makes an incision in the sample carrier. After the incision has been made, the portion of the sample carrier extending from the opening and not comprising sample material can be broken off and removed. The lid is moved from the open—i.e. the first—to the closed—i.e. the second—position and during that motion the cutter, for instance a cutting edge comprised in the lid, makes an incision in the sample carrier part of which can then be broken off and removed. The fact that a single motion performs both the closing of the opening receiving the sample carrier and the cutting of the sample carrier implies that the portion of the sample carrier comprising the sample material is always held under control; it is either attached to the sample carrier or sealed within its receiving receptacle. This makes the sample less prone to accidental contamination. Also, this single motion simplifies the manipulation of the device, which is a key benefit in point of care settings, and facilitates its integration in an automated environment as the number of steps to be performed as well as the number of parts that need to be accessed and manipulated is reduced. "Sealing" in the present context means closing the opening in such a way that the sample material inside the device is no longer accessible to the environment outside the device and, conversely, that the sample material inside the device cannot access (contaminate) the environment outside the device. This does not necessarily require an air tight seal between the interior of the device and the outside world although the housing of the device an/or the lid may preferably provide for means for effecting an air tight sealing between the interior and the exterior, for example using rubber seals. The opening does not need to be fully closed by the lid for a seal being effected. Although the opening being fully closed/covered by the lid is considered as beneficial embodiment of sealing, any other closing/coverage of the opening by the lid contributing to a seal is included in the present context of "effecting sealing", too. Advantageously, a part of the opening may be closed by the lid while another part of the opening may be closed by the remainder of the sample carrier as cut and retained in a press fit in such other part of the opening. In an embodiment, the lid is retained in its second position by appropriate means such as locking means or snapping means. Such means shall prevent any accidental re-opening of the device granting access to the sample material.

An embodiment of a device according to the present disclosure is characterized in that the cutter is formed by a cutting edge. This embodiment has the advantage that that it allows easy manufacturing.

A further embodiment of a device according to the present disclosure is characterized in that the cutting edge comprises or is made of polycarbonate. This embodiment has the advantage that polycarbonate is a suitable material for manufacturing a cutter which also allows easy manufacturability. In general any material, preferably a plastic that is sufficiently strong to make an incision in a sample carrier is suitable.

A further embodiment of a device according to the present disclosure is characterized in that the cutter is comprised in the lid. This embodiment has the advantage that it allows easy assembly.

A further embodiment of a device according to the present disclosure is characterized in that the device further comprises a support structure along which the lid is movable during at least part of its motion. This embodiment has the advantage that it allows easy guiding of the lid.

A further embodiment of a device according to the present disclosure is characterized in that the support structure is positioned at least on the side of the lid comprising the cutter.

This embodiment has the advantage that it limits access to the cutter, hence enhancing safety for a person handling the device.

A further embodiment of a device according to the present disclosure is characterized in that the cutter is comprised in a brim bounding the opening. This embodiment has the advantage that it allows more freedom in choosing the thickness of the lid which may be thinner if the cutter is comprised in the brim instead of the lid. This arrangement may be beneficial when using manufacturing techniques like cast molding.

A further embodiment of a device according to the present disclosure is characterized in that the cutting edge lies in the plane of the opening. This embodiment has the advantage that the position at which a sample carrier comprising an incision made by the cutting edge can be broken of his better defined than if, for instance, the cutting edge lies below the plane of the opening relative to the direction of receipt of the sample carrier. In the latter case the sample carrier will break somewhere above the cutting edge, that is between the cutting edge and the end of the sample carrier extending from the opening.

A further embodiment of a device according to the present disclosure is characterized in that the opening for receiving part of the sample carrier comprises a main part for receiving the sample carrier and an auxiliary part, the auxiliary part being adapted for retaining the sample carrier in position, the main part and the auxiliary part together forming a single opening.

This embodiment has the advantage that on the one hand the main part provides an opening large enough to easily put a sample carrier into the opening, while on the other hand the auxiliary part allows the sample carrier to be kept in a specific position. In this position, the cutter can be used to make an incision in the sample carrier. The auxiliary part may be adapted for keeping the sample carrier in position by having a diameter equal to or somewhat smaller than the diameter of at least part of the sample carrier so that the sample carrier can be squeezed into the auxiliary opening. Consequently, in a preferred embodiment the auxiliary part is designed for retaining a received sample carrier in a press fit. When being moved into such press fit in the auxiliary part, the sample carrier may be cut more easily. At the same time or even in an alternative embodiment independent from the existence of an auxiliary part the main part of the opening may be designed for holding a received sample carrier with backlash. This provides for an easy introduction of the sample carrier into the device. Advantageously, the diameter of the main part is larger than the largest diameter of the sample carrier allowing for a smooth insertion of the sample carrier without scraping the sample from the carrier during insertion. As a result, in another embodiment, the auxiliary part of the opening is smaller in its dimension than its main part.

In case of the opening providing a main part and an auxiliary part, it is advantageous that when being arranged in a closed position the lid closes the main part of the opening. This may enable a closure of that part of the opening that is used for receiving the sample carrier in the beginning before the sample carrier may be moved into a position corresponding to the auxiliary part of the opening for being cut. The auxiliary part finally may be covered/closed by the remainder of the sample carrier itself after cutting.

In addition, the closed lid may partially close the auxiliary part of the opening, too, in particular when a cutting edge of the lid is extending into the auxiliary part in the closed position of the lid. This further helps having the remainder of the sample carrier being retained in the position corresponding to the auxiliary part of the opening.

In another preferred embodiment, the lid is designed such that when moving the lid from an open position to a closed position with respect to the opening the sample carrier is forced into the auxiliary part of the opening. This helps reducing steps to be manually executed since simply by moving the lid all three actions may automatically be executed: moving the sample carrier into the auxiliary part of the opening; making an incision in the sample carrier; closing at least part of the opening.

A further embodiment of a device according to the present disclosure is characterized in that the lid is slidable or rotatable. This embodiment has the advantage that the two types of motion allow easy operation of a lid suitable for forcing a sample carrier and a cutter together.

A further embodiment of a device according to the present disclosure is characterized in that the device comprises a terminus for indicating the closed position of the lid. This embodiment has the advantage that the terminus provides an easy means for informing an operator of the device of whether or not the opening for receiving a sample carrier is fully closed. Closure of the device may be especially important if the chemical analysis involves hazardous chemical substances, which may include biological substances.

A further embodiment of a device according to the present disclosure is characterized in that the chemical analysis is a molecular diagnostics test. This embodiment has the advantage that molecular diagnostic tests would benefit from the present disclosure because devices into which sample carriers can be inserted through openings and which require subsequent removal of a part of the sample carriers and closing of the openings are often used within this context.

A further embodiment of a device according to the present disclosure is characterized in that the device is a cartridge, the cartridge being insertable into an instrument for processing the cartridge. This embodiment has the advantage that chemical tests, including molecular diagnostics tests, requiring inserting sample carriers through openings in devices for use in the tests, removing part of the sample carriers and closing the openings through which the sample carriers were inserted often involve cartridges that can be inserted into instruments for handling the cartridges. Consequently, such cartridges would benefit from the present disclosure.

When it comes to the shape of the lid and its arrangement in the device, the following preferred embodiments are disclosed:

The lid may be formed as a planar element with a length, a width and a height, and with each of the length and the width exceeding the height five times at minimum. This enables the device being embodied as a thin, small scale device. In a preferred embodiment, the device comprises a housing with a wall and the wall comprises a recessed portion. The opening is arranged in the recessed portion of the wall. The lid is movably arranged in the recessed portion. This enables the device being a thin, small scale device with a lid being easy to grip as an operator is in a position to simultaneously hold the device and operate the lid for closing the opening and/or the cutter for making an incision in the sample carrier. In particular, the recessed portion of the wall may comprise a planar top surface facing a planar bottom surface of the lid. It may also be advantageous that a height of the recess in the wall corresponds to a height of the lid. This supports building a thin, small scale device without the need for prominent support structures for the cutter. According to another embodiment, the lid comprises gripping means for supporting a manual moving of the lid. Such gripping means may be implemented as a handle or as a roughened part of the top surface of the lid for enabling the operator to move the lid. In another embodiment, a planar dimension of the lid—which is understood as an area defined by the length and the width of the planar lid—is smaller than a planar dimension of the recessed portion of the wall—again understood as the length and the width of the recessed portion.

The object of the present disclosure is further realized with a system as disclosed herein. The above-mentioned system would benefit from any one of the previous embodiment.

The object of the present disclosure is further realized with a method for making an incision in a sample carrier. The method can include the steps of: placing the sample carrier in an opening for receiving the sample carrier; and making an incision in the part of the sample carrier extending from the opening using a cutter. In the step of making an incision, the incision is made by moving a lid from a position in which the opening is open to a position in which at least part of the opening is closed.

In a preferred embodiment, the lid is designed such that in a closed position at least part of the opening left open by the sample carrier after receipt of the sample carrier by the opening is closed.

The described embodiments similarly pertain to the device, the system, and the method. Synergetic effects may arise from different combinations of the embodiments although they might not be described in detail.

BRIEF DESCRIPTION OF THE DRAWINGS

The aspects defined above and further aspects, features and advantages of the present disclosure can also be derived from the examples of embodiments to be described hereinafter and are explained with reference to examples of embodiments. The present disclosure will be described in more detail hereinafter with reference of examples of embodiments but to which the present disclosure is not limited.

FIGS. 1a through 1d schematically show an embodiment of a device according to the present disclosure;

DETAILED DESCRIPTION OF EMBODIMENTS

Figure 2:
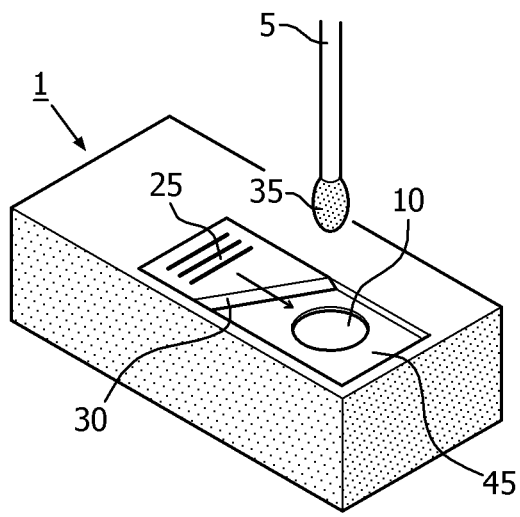
FIG. 2 schematically shows a further embodiment of a device according to the present disclosure.

FIGS. 1a through 1d schematically show an embodiment of a device according to the present disclosure. FIG. 1 shows a device 1 which may be a cartridge insertable into an instrument for handling the cartridge. The cartridge may be a molecular diagnostics cartridge for testing, for instance, a saliva or stool sample. The cartridge is insertable into an instrument suitable for processing a sample in the cartridge in the sense that the instrument may provide, for instance, heating, cooling, cell lysis, and data acquisition services for the sample in the cartridge.

FIG. 1 further shows a sample carrier 5 which is, in this case, a swab. Alternatively, the sample carrier may be a brush, a stick, etc. Usually, the sample carrier 5 has a rodlike shape. The device 1 comprises an opening 10 for receiving the sample carrier 5. The arrow in FIG. 1a indicates the sample carrier 5 moving towards and partially into the opening 10. In this particular embodiment, the opening 10 comprises a main part 15, through which the sample carrier 5 enters the device 1, and an auxiliary part 20 being adapted for keeping the sample carrier 5 in a specific position. In this case, the dimensions of the auxiliary part 20 are such that the sample carrier 5 closely fits within the auxiliary part 20. Consequently, the sample carrier 5 can be positioned in the auxiliary part 20 after which the sample carrier 5 is kept in its position by the auxiliary part 20 due to the dimensions of one relative to the other. However, for the present disclosure the presence of an auxiliary part 20 is not necessary.

The device 1 further comprises a lid 25. The lid 25 is slidable as indicated by the arrow in FIG. 1b. In this particular embodiment, the lid 25 comprises a cutting edge 30 which functions as a cutter. When translating the lid 25, the cutting edge 30 makes an incision in a portion of the sample carrier 5 that is extending from the opening 10 and that does not hold sample material. Sample material is present on the tip 35 of the sample carrier 5 (see FIG. 1a). Simultaneously with making the incision, the lid 25 closes at least that part of the opening 10—i.e. in the present embodiment especially the main part 15 of the opening 10—that is left open after insertion of the sample carrier 5 into the opening 10.

After the incision has been made, the portion of the sample carrier 5 extending from the opening 10 can be broken off and removed. This is shown in FIG. 1c. FIG. 1d shows the device 1 with the lid 25 in the closed position. The lid 25 closes the main part 15 of the opening 10 and part of the auxiliary opening 20. The auxiliary opening 20 per se is closed by the portion of the sample carrier 5 remaining in the device 1 after the part of the sample carrier 5 that originally extended from the opening 10 has been broken off and removed. The piece of the sample carrier 5 that has been broken off and removed is shown next to the device 1.

FIGS. 1a through 1d further shows a support structure 40. This support structure of 40 guides the lid 25. However, the support structure 40 also limits access to the cutting edge 30 comprised in the lid 25. In the present embodiment, limiting the access to the cutting edge 30 by the support structure 40 is accomplished on the one hand by having the support structure 40 next to the cutting edge 30 when the lid 25 is in the open position (FIG. 1a) and on the other hand by shaping the support structure of 40 in relief. Either of these two measures may be sufficient to limit access to the cutting edge 30. The lid 25 and the opening 10 are located in an area 45 the surface of which is positioned nearer to the interior of the device 1 than the rest of the surface of the device 1 facing the sample carrier 5 in FIG. 1a, i.e. the surface of the cartridge may be recessed in this area 45. In this embodiment, the support structure 40 is basically formed by a brim surrounding the area 45.

FIG. 2 schematically shows a further embodiment of a device according to the present disclosure. FIG. 2 basically shows the same device as shown in FIG. 1a. Corresponding elements have been given the same reference numerals as in FIGS. 1a through 1d. However, in FIG. 2 there is no auxiliary part 20 of the opening 10. This only serves to illustrate that an auxiliary part 20 is not necessary for the present disclosure in general. Of course, a device according to the present disclosure may be adapted to comprise an auxiliary part 20 as well. The cutting edge 30 comprised in the lid 25 faces in the direction of motion of the lid 25 as indicated by the arrow.

Again, a sample carrier 5 can be inserted into the opening 10. After the sample carrier 5 has been inserted into the opening 10, the lid 25 is moved towards the opening 10. Once the lid 25 starts to cover the opening 10 the cutting edge 30 starts to make an incision in a part of the sample carrier 5 extending from the opening 10. Once the sample carrier 5 has been sufficiently weakened by the incision, the portion of the sample carrier 5 extending from the opening 10 can be broken off and removed similar to the procedure shown in FIG. 1. However, in the present embodiment, the lid 25 is able to completely cover the opening 10. This is a result of the cutter, in this case the cutting edge 30, being arranged in the direction of motion of the lid 25. In the present embodiment, the cutting edge 30 is inclined at an angle different from 90° relative to the direction of motion of the lid 25. This enhances the cutting function. As with all embodiments of the present disclosure, the cutting edge 30 or, more generally, the cutter may be serrated (not shown).

Figure 3A:
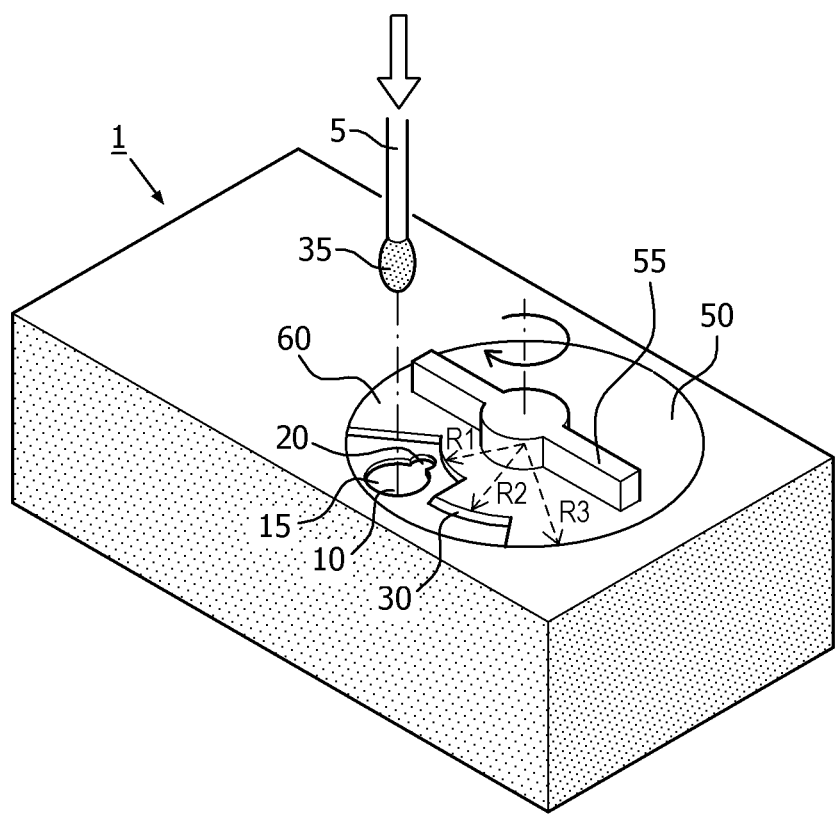
FIGS. 3a through 3c schematically show a further embodiment of a device according to the present disclosure.
Figure 3B:
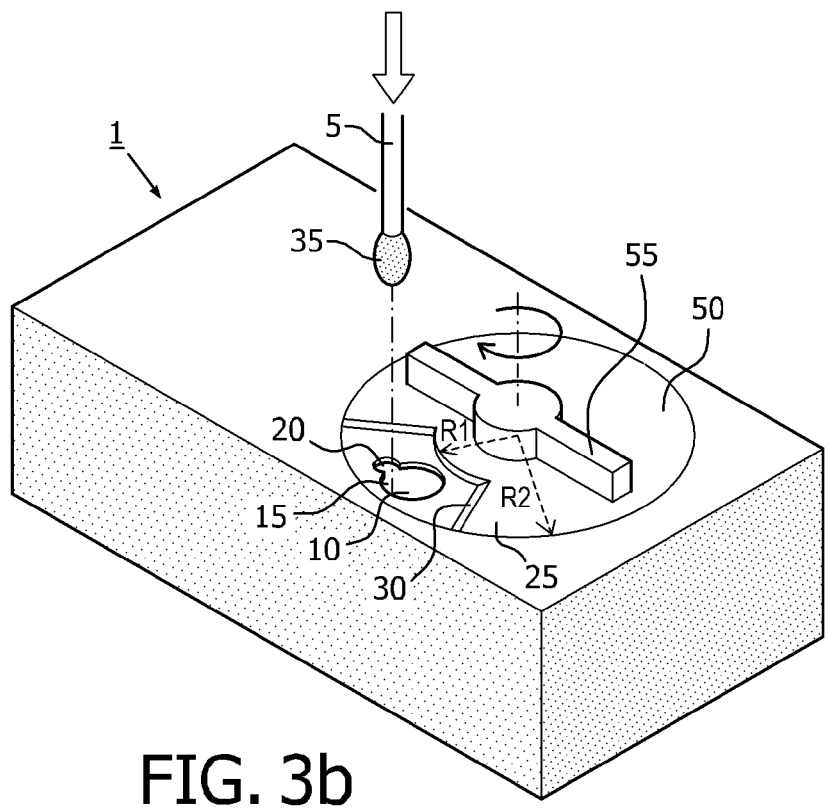
Figure 3C:
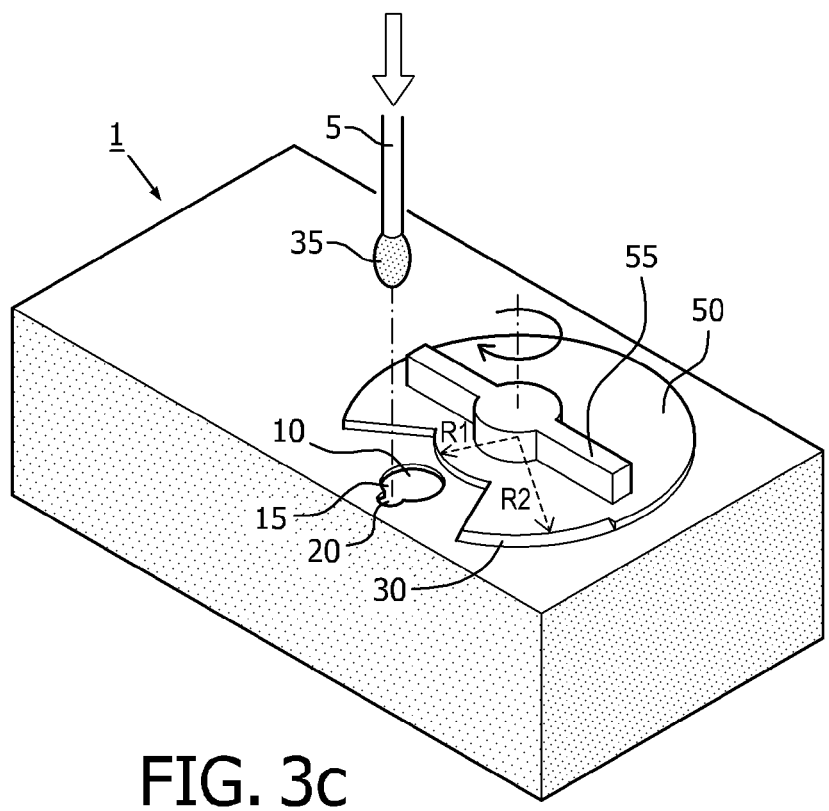

FIG. 3a through 3c schematically show further embodiments of devices according to the present disclosure. FIGS. 3a through 3c show devices similar to those shown in FIGS. 1 and 2. Similar elements have been given identical reference numerals. However, in FIGS. 3a through 3c, a rotational motion is used to make an incision in a sample carrier rather than a translational motion as in FIGS. 1 and 2.

In FIG. 3a, the device 1 comprises a rotatable lid 50. The rotatable lid 50 comprises a grip 55 allowing the lid 50 to be rotated around the axis indicated by the dashed line. The device 1 comprises an opening 10 for receiving a sample carrier 5. The opening 10 comprises a main part 15 and an auxiliary part 20 just as in FIG. 1. However, as already shown in FIG. 2 this is not mandatory.

The auxiliary part 20 is orientated towards the axis of rotation of the lid 50, i.e. it is arranged closer to the center of the lid 50 than the main part 15. The lid 50 further comprises a disk 60. The disk 60 comprises different areas having different radii. The first area with radius R1 leaves the opening 10 open to receive sample carrier 5. The second area has a radius R2 which is larger than R1. The second area with radius R2 forms a cutter in that the second area comprises a cutting edge 30. Radius R2 is such that the cutting edge 30 makes an incision into the sample carrier 5 when the second area moves along the sample carrier 5. After the incision has been made, the part of the sample carrier 5 that extends from the device 1 can be broken off and removed just as in FIGS. 1 and 2. After that, the lid 50 can be rotated further such that the third area with radius R3, R3 being larger than R2, completely covers the opening 10.

FIG. 3b shows a device 1 similar to that shown in FIG. 3a. Again, similar elements have been given identical reference numerals. However, this time the auxiliary part 20 of the opening 10 is circumferentially arranged next to the main part 15 such that when the lid 50 rotates it hits the main part 15 and the auxiliary part 20 subsequently. The lid 50 comprises a first area with radius R1 such that this first area leaves the opening 10 open for receiving a sample carrier 5. The lid 50 further comprises a cutting area 65 comprising a cutting edge 30 similar to the cutting edge 30 shown in FIG. 2. As the lid 50 rotates in the direction indicated, the cutting edge 30 engages the sample carrier 5. Again, an incision is made in the sample carrier 5 after which the part of the sample carrier 5 extending from the device 1 can be broken off and removed. After that, the lid 50 can be rotated further such that a second area with radius R2, R2 being larger than R1, completely covers the opening 10.

FIG. 3c shows a device 1 similar to the devices shown in FIGS. 3a and 3b. Again, similar elements have been given identical reference numerals. In the present embodiment, the auxiliary opening 20 is orientated away from the axis of rotation of the lid 50, i.e. it is arranged farther from the center of the lid 50 than the main part 15. This arrangement has the advantage that the lid 50 tends to push the sample carrier 5 into the auxiliary part 20 of the opening 10 when the lid 50 forces the cutting edge 30 and the sample carrier 5 together.

The lid 50 comprises a first area with a radius R1 such that it leaves the opening 10 open for receiving a sample carrier 5. The lid 50 further comprises a second area with radius R2, R2 being larger than R1. The second area comprises the cutting edge 30. R2 is such that the cutting edge 30 is able to make an incision in the sample carrier 5 when the cutting edge 30 passes along and partially over the auxiliary part 20 in which the sample carrier 5 is kept in a fixed position. Again, after the incision has been made the part of the sample carrier 5 extending from the device 1 can be broken off and removed. If the lid 50 is rotated over a sufficient angle, the second area of the lid 50 is able to completely cover the main part 15 of the opening 10. The auxiliary part 20 of the opening 10 is closed by the part of the sample carrier 5 that remains with a device 1 after the rest of the sample carrier 5 has been broken off and removed. Alternatively, the lid 50 may further comprise a third area with radius R3 (not shown), R3 being larger than R2 (see for instance FIG. 3a for an analogous situation). If R3 is large enough the lid 50 may be rotated such that the third area with radius R3 covers both the main part 15 and the auxiliary part 20 of the opening 10 after an incision has been made in the sample carrier 5.

Figure 4A:
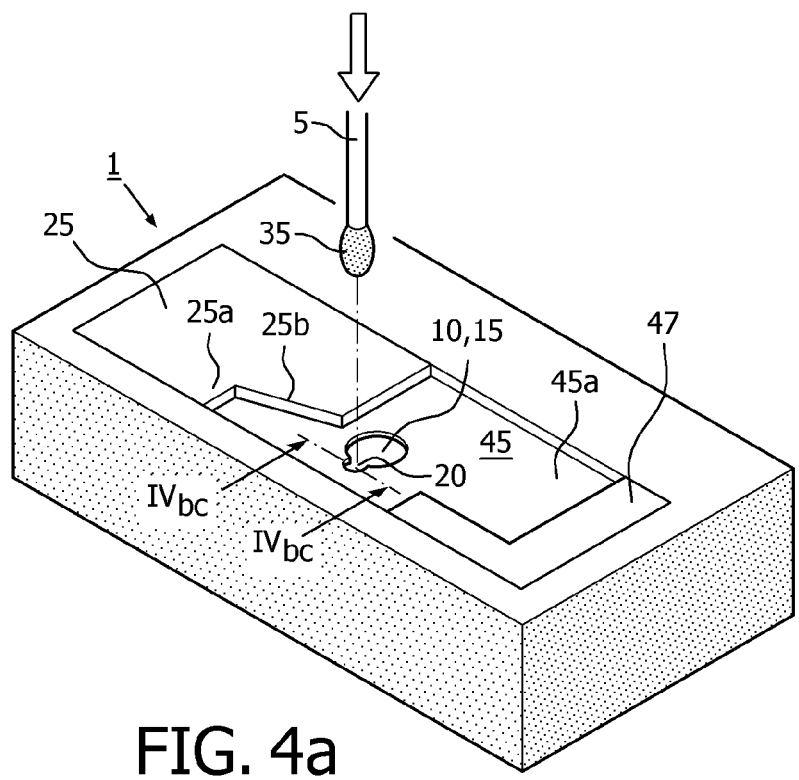
FIGS. 4a through 4c schematically show a further embodiment of a device according to the present disclosure.
Figure 4B:
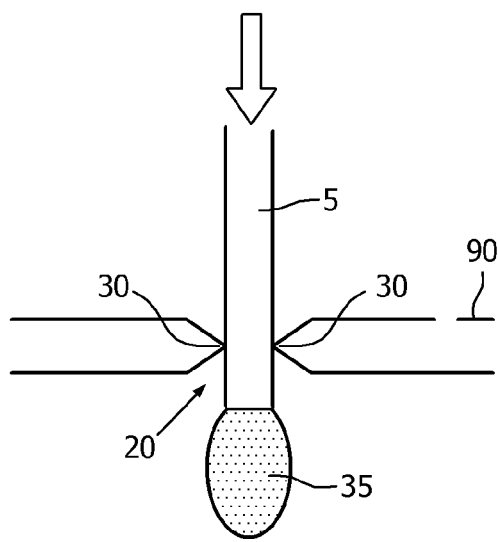
Figure 4C:
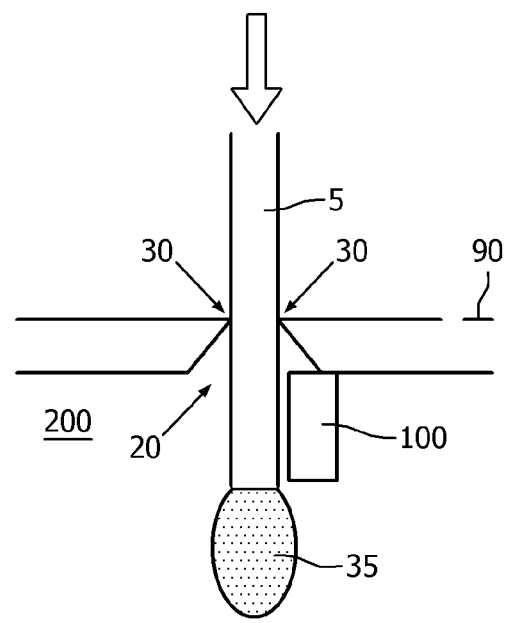

FIGS. 4a through 4c schematically show further embodiments of a device according to the present disclosure.

FIG. 4a shows a device similar to the device 1 shown in FIG. 1. Again, similar elements have been given identical reference numerals. However, the device 1 in the present figure comprises a number of features not shown in FIG. 1. It will be obvious to a person skilled in the art any of that these features of the present figure may be combined with the device shown in the other figures.

In FIG. 4a the cutting edge is comprised in the brim of the auxiliary part 20 of the opening 10 instead of in the lid 25. This allows greater freedom in choosing the thickness of the lid 25 which may be beneficial when employing manufacturing methods such as cast molding. If, for instance, a lid comprising a cutting edge becomes too thin, it might bend when forcing a sample carrier and a cutting edge together due to the surface of the cutting edge being inclined at a non-90° angle relative to the direction of motion of the lid while the sample carrier is at 90° relative to this direction.

FIG. 4a further shows a lid 25 that has an additional appendage 25a as compared to the lid 25 shown in FIG. 1. With the additional appendage 25a the lid 25 is able to cover both the main part 15 and the auxiliary part 20 of the opening 10 if the lid 25 is moved far enough from the open position towards the closed position.

The lid 25 shown in the present figure further comprises an area 25b the brim of which is inclined at a non-90° angle relative to the direction of motion of the lid 25. Consequently, when moving the lid 25 to the closed position, the narrower end of the area 25b passes by the sample carrier 5 in the auxiliary part 20 of the opening 10 until the inclined brim of the area 25b contacts the sample carrier 5. From that point on, the inclined brim of the area 25b pushes the sample carrier 5 into the auxiliary part 20 of the opening 10.

If the dimensions of the auxiliary part 20 are such that they allow the sample carrier 5 to move further into the auxiliary part 20, pushing with the inclined brim of the area 25b will lead to the sample carrier 5 moving along the cutting edge 30 comprised in the brim of the auxiliary part 20. Motion of the sample carrier 5 along the cutting edge 30 further enhances the making of an incision by the cutting edge 30 into the sample carrier 5. This can be achieved with, for instance, an auxiliary part 20 that extends like a slit (not shown) from the main part 15 of the opening 10. The width of the auxiliary part 20 and the width of a sample carrier 5 are then such that they together allow the sample carrier 5 to be fixed in a specific orientation in the auxiliary part 20, while the slit forming the auxiliary part 20 is long enough to allow the sample carrier 5 to move further from the main part 15 into the slit under the pushing force exerted using the inclined brim of the area 25b. In short, the inclined brim of the area 25b is used to push the sample carrier 5 further into the auxiliary part 20 resulting in the sample carrier 5 moving along the cutting edge 30 comprised in the brim of the auxiliary part 20.

The auxiliary part 20 of the opening 10 may be shaped to further facilitate keeping a sample carrier in a fixed position once the sample carrier is inserted into the auxiliary part. To this end, the auxiliary part may become narrower (not shown) going from the position at which the auxiliary part 20 is coupled to the main part 15 to the closed end of the auxiliary part.

The shape of the area 45a is complimentary to part of the shape of the lid 25. Consequently, the brim of the area 45a forms a terminus for the movement of the lid 25 from the open to the closed position. If the lid 25 is moved against the brim of the area 45a an operator of the device 1 can be sure that the opening 10 is fully closed. Ensuring that the opening 10 is closed is especially relevant if the device 1 or the sample carried by the sample carrier 5 comprise hazardous materials such as chemical or biological substances. A color coding may be applied to the lid 25, the area 45a, and/or the area 47 to indicate that the lid 25 has reached the closed position. The lid 25 and the area 47 may, for instance, be given a color (that may be the same for the lid 25 and the area 47) that is different from the color of the area of 45a. As long as the color of the area 45a is still visible, the lid 25 has not yet reached the closed position. It will be clear to the skilled person that the terminus may be provided in different forms. As an alternative to the embodiment shown in the present figure, the area 45a might comprise a protrusion which the lid 25 touches in the closed position. The lid 25 might also comprise an indentation the shape of which is complimentary to the shape of the protrusion.

FIG. 4b schematically shows an embodiment of the cutting edge 30 for the device 1 shown in FIG. 4a as viewed along the line IVbc-IVbc in FIG. 4a. The cutting edge lies below a top plane 90 defining the auxiliary part 20 of the opening 10 relative to the direction of receipt of the sample carrier.

FIG. 4c schematically shows a preferred embodiment of the cutting edge 30 for the device 1 shown in FIG. 4a as viewed along the line IVbc-IVbc in FIG. 4a. The cutting edge 30 now lies in the top plane 90 defining the auxiliary part 20 of the opening 10. This embodiment has the advantage that the position at which the sample carrier 5 can be broken off after an incision has been made by the cutting edge 30 is better defined than with the cutting edge 30 shown in FIG. 4b. In the present embodiment, the sample carrier 5 will break at the position of the cutting edge 30 if the sample carrier 5 is sufficiently bent after an incision has been made by the cutting edge 30. In FIG. 4b the sample carrier 5 might break somewhere above the cutting edge 30 because in that arrangement the sample carrier 5 has more room to bend as indicated by the dashed lines in that figure.

FIG. 4c further shows a support 100 for limiting the motion of the sample carrier 5 during the making of an incision in the sample carrier 5 or during bending of the sample carrier 5 in order to break it after an incision has been made. This support 100 may or may not extend along the whole length of the part of the sample carrier 5 that has been inserted into a device according to an embodiment of the present disclosure. In the present figure, the support 100 limits bending of the inserted part of the sample carrier 5 when the part of the sample carrier 5 that extends from the device is bended towards the left of the figure. To limit bending in another direction, the support 100 should be positioned in a correspondingly different location from the one shown in the present figure as will be clear to a person skilled in the art. If the part of the sample carrier 5 that extends from the device is bent towards the right of the figure, the support 100 should be positioned left of the opening of the auxiliary part 20 instead of to the right as shown in FIG. 4c. The support 100 may extend from the brim of the auxiliary part 20 into a device according to an embodiment of the present disclosure. As an alternative or in addition to the support 100 shown in the present figure, motion of the sample carrier 5 may be limited by a wall portion comprised in the wall defining the volume into which a sample carrier 5 is inserted. In that case, the support 100 shown in the present figure may be comprised in a wall bounding the volume 200 into which the sample carrier 5 has been inserted. Alternatively or in addition, motion of a sample carrier 5 may be limited both by a dedicated support 100 and a wall portion comprised in the wall defining the volume into which the sample carrier 5 is inserted. In that case, the support 100 may limit motion in one direction whereas the wall portion limits motion in another direction.

Figure 5:
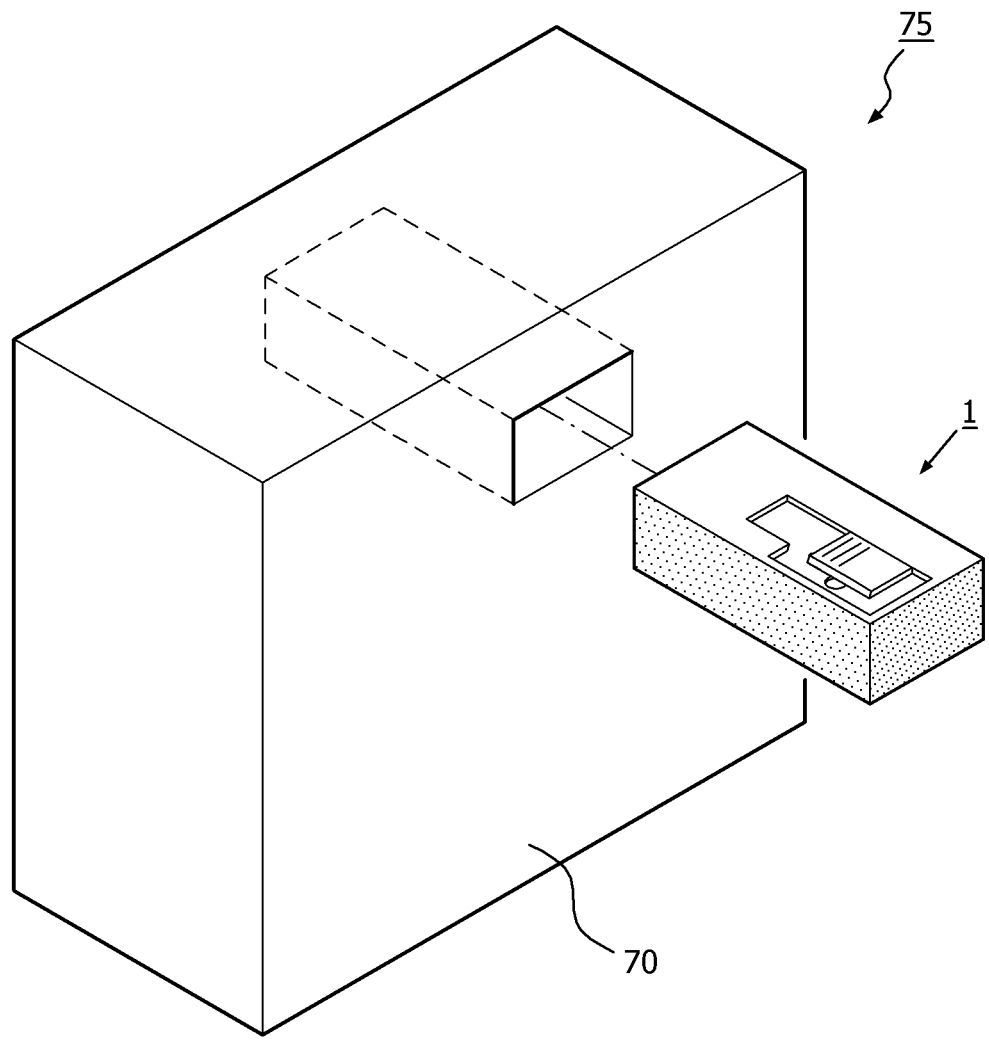
FIG. 5 schematically shows an embodiment of a system according to the present disclosure.

FIG. 5 schematically shows an embodiment of a system according to the present disclosure. The present figure shows a device 1 similar to the devices shown in any of the previous figures. In this particular embodiment, the device 1 is identical to the device 1 shown in FIG. 1d. Also shown is an instrument 70 for receiving and handling the device 1. The system 75 comprises the instrument 70 and the device 1. In this embodiment, the device 1 forms a cartridge that can be inserted into the instrument 70 after part of a sample carrier that has been used to provide the device 1 with sample material has been broken off and removed following the procedure outlined in the previous figures. The device 1 may hold the ingredients for performing a chemical reaction, whereas the instrument 70 provides facilities for performing and detecting the chemical reaction. The instrument 70 may provide, for instance, heating, cooling, cell lysis, and data acquisition facilities to the device 1. The device 1 may be a cartridge for detecting the presence of one or more pathogens in a sample, for instance a saliva, stool, or blood sample inserted into the device 1 using a sample carrier as shown in the previous figures. Different cartridges, that are different devices 1, may be inserted into the instrument 70 for performing different tests.

Figure 6:
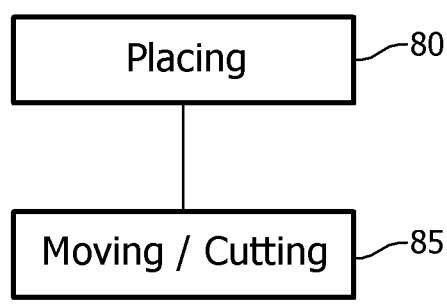
FIG. 6 schematically shows an embodiment of a method according to the present disclosure.

FIG. 6 schematically shows an embodiment of a method according to the present disclosure. In step 80 a sample carrier is placed in an opening comprised in a device for receiving the sample carrier. Next, in step 85, a lid is moved from a position in which the opening is open to a position in which the opening is closed. During this motion, the lid engages the sample carrier with a cutter which makes an incision in the sample carrier. Once the incision has been made, the part of the sample carrier at that extends from the device through the opening can be broken off and removed.

It should be noted that the above-mentioned embodiments illustrate rather than limit the present disclosure, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. In the system claims enumerating several means, several of these means can be embodied by one and the same item of computer readable software or hardware. The mere fact that certain measures are recited in mutually different dependent claims does not indicate that a combination of these measures cannot be used to advantage.

What is claimed is:

1. A device for use in chemical analysis of sample material, the device comprising:
   a housing comprised of a plurality of walls defining an inner volume, said plurality of walls including a first wall having an opening formed therein, wherein said opening is configured to receive at least part of a sample carrier having the sample material to be analyzed;
   a cutting edge that functions as a cutter for making an incision in the sample carrier; and
   a lid slidable in a moving path across the first wall from a first position to a second position that seals the opening, wherein when in the second position, at least part of the opening is closed by the lid, and wherein movement of the lid in the moving path forces the sample carrier into contact with the cutter wherein the cutting edge is formed on an edge of the lid or on a brim bounding the opening.

2. The device as claimed in claim 1, wherein the cutting edge is comprised of polycarbonate.

3. The device as claimed in claim 1, wherein the device further comprises a support structure along which the lid is slidable during at least part of the moving path.

4. The device as claimed in claim 3, wherein the support structure is positioned at least on a side of the lid.

5. The device as claimed in claim 1, wherein the cutting edge lies in a plane of the opening.

6. The device as claimed in claim 1, wherein the opening comprises a main opening part configured to receive a portion of the sample carrier and an auxiliary opening part adapted to retain the sample carrier in a desired position, the main opening part and the auxiliary opening part together forming a single opening.

7. The device as claimed in claim 6, wherein the auxiliary opening part is smaller than the main opening part.

8. The device as claimed in claim 6, wherein the auxiliary opening part retains the sample carrier in a press fit, and the main opening part holds the carrier from backlash.

9. The device as claimed in claim 6, wherein, when the lid is in the second position, the main opening part of said opening is closed by the lid.

10. The device as claimed in claim 6, wherein, when the lid is in the second position, the auxiliary opening part of said opening is not entirely covered by the lid.

11. The device as claimed in claim 1, wherein the lid is slidable in the moving path by a translation motion or a rotation motion.

12. The device as claimed in claim 1, further comprising a terminus for indicating the second position of the lid.

13. The device as claimed in claim 1, wherein the chemical analysis is a molecular diagnostics test.

14. The device as claimed in claim 1, wherein the device is a cartridge, the cartridge being insertable into an instrument for processing the cartridge.

15. The device as claimed in claim 1, wherein the lid is a generally planar element having a length, a width and a height, wherein each of the length and the width exceeds, at minimum, five times the height.

16. The device as claimed in claim 1, wherein the first wall includes a recessed portion, the opening being arranged in the recessed portion of the first wall, and the lid being movably arranged in the recessed portion.

17. The device as claimed in claim 16, wherein the recess has a height that corresponds to a height of the lid.

18. The device as claimed in claim 17, wherein the lid comprises a grip that assists manual movement of the lid.

19. The device as claimed in claim 16, wherein the lid has a planar dimension that is smaller than a planar dimension of the recessed portion of the wall.

20. The device as claimed in claim 16, wherein the lid has a planar bottom surface, the recessed portion of the first wall has a planar top surface, and the planar bottom surface of the lid is arranged on the planar top surface of the recessed portion of the first wall.

21. The device as claimed in claims 1, wherein the lid seals the opening by either closing the opening completely or closing a part of the opening that is left open by the sample carrier when received within the opening.

22. The device as claimed in claim 1, further comprising a retainer to retain the lid in the second position.

23. A system comprising:
    an instrument for use in the molecular analysis of a sample material;
    a cartridge that is received in the instrument, wherein the cartridge comprises:
       a housing comprised of a plurality of walls defining an inner volume, said plurality of walls including a first wall having an opening formed therein,
       a cutting edge that function as a cutter, and
       a lid slidable in a moving path across the first wall,
       wherein the opening is configured to receive at least part of a sample carrier having the sample material to be analyzed,
       wherein the cutting edge is formed by an edge of the movable lid so that movement of the lid from a first position in which the opening is open to receive the sample carrier to a second position in which the opening is at least partially closed forces the cutting edge into contact with the sample carrier.

24. A method for making an incision in a sample carrier comprising the steps of:
    placing the sample carrier in an opening of a cartridge, said opening formed in a first wall of the cartridge; and
    making the incision in the sample carrier by sliding a lid in a moving path across the first wall of the cartridge, from a first position in which the opening is open for receiving the sample carrier to a second position in which at least part of the opening is closed, wherein moving of the lid to the second position seals the opening.

25. The device as claimed in claim 1, wherein the moving path is a straight line or a curved line.

* * * * *

UNITED STATES PATENT AND TRADEMARK OFFICE
CERTIFICATE OF CORRECTION

PATENT NO. : 8,512,637 B2  
APPLICATION NO. : 13/289534  
DATED : August 20, 2013  
INVENTOR(S) : Zeijlstra et al.

Page 1 of 1

It is certified that error appears in the above-identified patent and that said Letters Patent is hereby corrected as shown below:

On title page, insert item (30) Foreign Application Priority Data,

--May 6, 2009   (EP) 09159492.9--

Signed and Sealed this  
Eighth Day of October, 2013

Teresa Stanek Rea  
*Deputy Director of the United States Patent and Trademark Office*